(12) United States Patent
Mada

(10) Patent No.: US 9,770,770 B2
(45) Date of Patent: Sep. 26, 2017

(54) RIGID UNIVERSAL CARTRIDGE FOR HOLDING SYSTEM

(71) Applicant: Vijay Kumar Mada, Bangalore (IN)

(72) Inventor: Vijay Kumar Mada, Bangalore (IN)

( * ) Notice: Subject to any disclaimer, the term of this patent is extended or adjusted under 35 U.S.C. 154(b) by 0 days.

(21) Appl. No.: 15/008,485

(22) Filed: Jan. 28, 2016

(65) Prior Publication Data

US 2016/0136740 A1    May 19, 2016

Related U.S. Application Data

(63) Continuation of application No. 14/115,876, filed as application No. PCT/IN2012/000750 on Nov. 15, 2012.

(51) Int. Cl.
B23C 5/24 (2006.01)
B23B 29/034 (2006.01)

(52) U.S. Cl.
CPC ........ B23C 5/2472 (2013.01); B23B 29/0341 (2013.01); B23C 5/241 (2013.01); B23C 5/2489 (2013.01); B23B 2260/056 (2013.01); B23C 2226/125 (2013.01); B23C 2226/315 (2013.01); B23C 2250/16 (2013.01)

(58) Field of Classification Search
CPC ........... B23C 5/22; B23C 5/24; B23C 5/2472; B23C 2226/125; B23C 2226/315; B23C 2250/16; B23C 5/241; B23C 5/2489; B23B 29/0341; B23B 2260/056; C07B 2200/07
USPC .............................................. 407/36, 38, 39
See application file for complete search history.

(56) References Cited

U.S. PATENT DOCUMENTS

| 948,269 | A | * | 2/1910 | Crowley | ................. B23B 51/00 175/413 |
| 1,438,876 | A | * | 12/1922 | Thomas | ................... E21B 10/12 122/20 B |
| 1,790,613 | A | * | 1/1931 | Gildersleeve et al. | . E21B 10/12 175/348 |
| 1,812,475 | A | * | 6/1931 | Gildersleeve | ........... E21B 10/12 175/347 |
| 1,945,854 | A | * | 2/1934 | Hall | .......................... B23C 5/22 407/39 |

(Continued)

FOREIGN PATENT DOCUMENTS

| DE | FR 2252887 A1 | * | 6/1975 | ......... B23B 29/0341 |
| JP | 02160405 A | * | 6/1990 | ....... B23B 29/03407 |
| SE | EP 0332596 A2 | * | 9/1989 | ........... B23C 5/2441 |

*Primary Examiner* — Sara Addisu

(57) ABSTRACT

The present invention provides a rigid cartridge for multiple and universal application of all machining processes. The rigid cartridge includes a cylindrical body, a guiding and locating body connected to bottom side of cylindrical body, and a combination screw having a left hand [LH] thread and a right hand [RH] thread, wherein the cylindrical body includes a flat for locking the cartridge with the cutter body using locking screws, wherein the combination screw is connected to the bottom end of said guiding and locating body. The LH thread can be provided in cartridge side and RH thread can be provided in cutter body side or vice versa. In the cutter body or boring bar, a slot and/or approach hole can be provided in the cutter body for enabling to rotate the combination screw in clockwise or anti-clockwise direction to move the cartridge in forward and backward direction with respect to the cutter body.

10 Claims, 7 Drawing Sheets

(56) References Cited

U.S. PATENT DOCUMENTS

| | | | | |
|---|---|---|---|---|
| 1,952,996 A * | 3/1934 | Landgraf | E21B 17/042 | 403/299 |
| 2,125,005 A * | 7/1938 | Jearum | B23B 29/0341 | 125/39 |
| 2,418,734 A * | 4/1947 | Steffes | B23B 27/1685 | 407/110 |
| 2,524,374 A * | 10/1950 | Briney, Jr. | B23B 29/03407 | 408/181 |
| 2,586,955 A * | 2/1952 | Kaiser | B23C 5/242 | 407/38 |
| 2,800,041 A * | 7/1957 | Sten | B23B 27/18 | 403/104 |
| 2,862,286 A * | 12/1958 | Williams | B23C 5/242 | 407/38 |
| 2,913,935 A * | 11/1959 | Flannery | B23B 29/0341 | 279/42 |
| 3,073,186 A * | 1/1963 | Flannery | B23B 29/0341 | 408/116 |
| 3,195,376 A * | 7/1965 | Bader | B23C 5/2441 | 407/49 |
| 3,262,184 A * | 7/1966 | Sweeny | B23B 29/0341 | 407/73 |
| 3,349,648 A * | 10/1967 | Holloway | B23B 29/0341 | 408/154 |
| 3,400,616 A * | 9/1968 | Mihic | B23B 29/0341 | 408/146 |
| 3,447,403 A * | 6/1969 | Vogel, Sr. | B23B 29/0341 | 408/146 |
| 3,521,507 A * | 7/1970 | Yogus | B23B 29/03407 | 407/37 |
| 3,697,187 A * | 10/1972 | Faber | B23B 29/0341 | 408/154 |
| 3,741,672 A * | 6/1973 | Hedberg | B23B 29/034 | 408/146 |
| 3,767,317 A * | 10/1973 | Ortlieb | B23B 29/034 | 408/183 |
| 3,796,464 A * | 3/1974 | Hansen | E21C 35/1933 | 299/104 |
| 3,844,009 A * | 10/1974 | Anania | B23B 29/26 | 407/113 |
| 4,018,112 A * | 4/1977 | Heaton | B23B 29/20 | 408/35 |
| 4,135,846 A * | 1/1979 | Nowakowski | B23B 5/163 | 408/157 |
| 4,157,879 A * | 6/1979 | Steele | B23B 5/167 | 408/227 |
| 4,222,446 A * | 9/1980 | Vasek | E21C 35/183 | 175/413 |
| 4,278,372 A * | 7/1981 | Heisner | B23B 29/03417 | 407/45 |
| 4,511,006 A * | 4/1985 | Grainger | B21K 25/00 | 175/354 |
| 4,629,374 A * | 12/1986 | Berner | B23B 31/113 | 279/7 |
| 4,799,838 A * | 1/1989 | Kubo | B23B 31/028 | 279/156 |
| 4,893,967 A * | 1/1990 | Briese | B23C 5/22 | 407/101 |
| 4,964,763 A * | 10/1990 | Kieninger | B23C 5/207 | 407/101 |
| 4,971,491 A * | 11/1990 | Cook | B23B 31/006 | 408/1 BD |
| 5,152,541 A * | 10/1992 | Baumgartner | B23B 31/02 | 279/20 |
| 5,454,667 A * | 10/1995 | Cirino | B23B 29/0341 | 408/153 |
| 6,254,319 B1 * | 7/2001 | Maier | B23C 5/2444 | 407/45 |
| 8,327,742 B1 * | 12/2012 | Austin | B23C 5/2472 | 407/37 |
| 2013/0175769 A1 * | 7/2013 | Yang | B23B 31/028 | 279/105.1 |
| 2016/0089730 A1 * | 3/2016 | Kocherovsky | B23C 5/2472 | 407/88 |

* cited by examiner

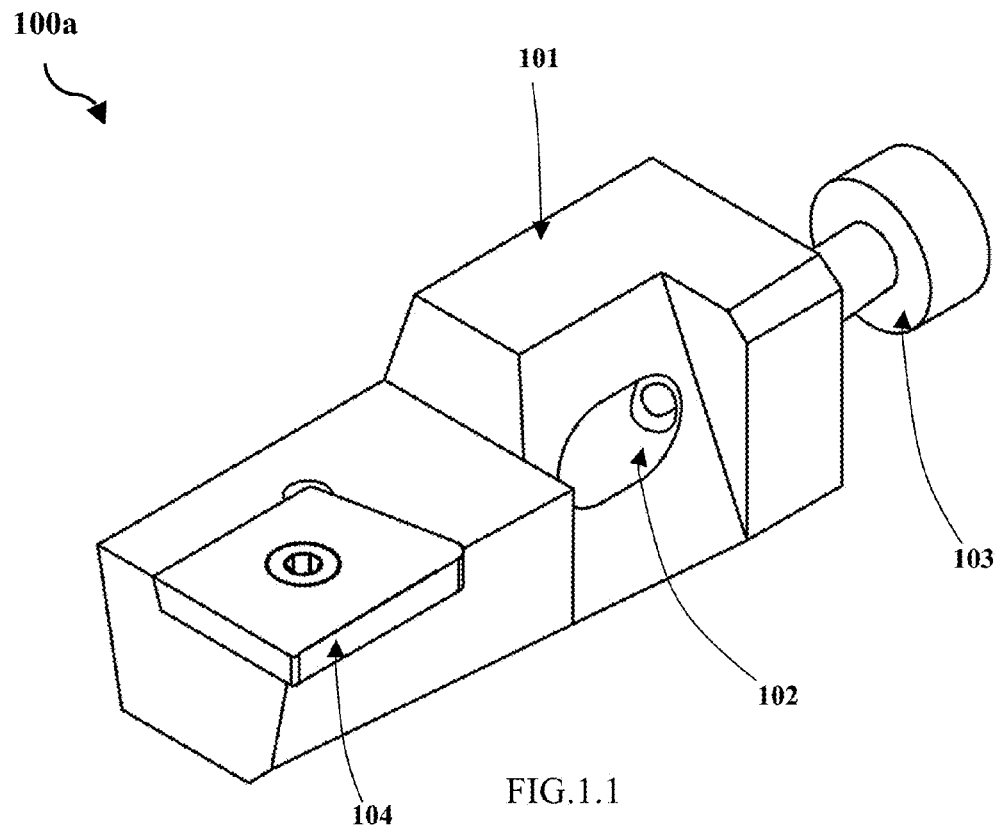
FIG.1.1
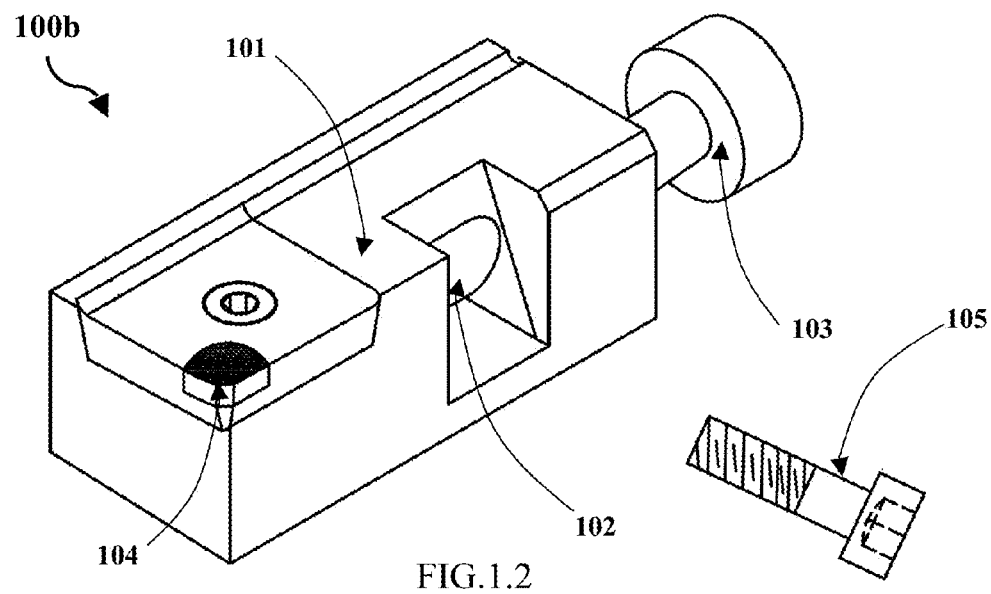
FIG.1.2

RIGID UNIVERSAL CARTRIDGE FOR HOLDING SYSTEM

FIELD OF INVENTION

The embodiments herein generally relate to the field of machining process, more specifically, it relates to a novel rigid universal cylindrical cartridge for holding system, which can control in microns axially and radially in all type of machining process.

BACKGROUND OF THE INVENTION

Milling cutters and boring bars are tools typically used in milling machines and metalworking, wherein the milling cutters used for cutting work pieces and boring bars used to create a slot or asymmetrical hole or channel, or to create a perfect circular hole. The milling cutters generally comprise a cylindrical cutter body having a spindle on one side for attachment to a source of rotary power, and a plurality of cutting inserts mounted around the outer side of the body for cutting a work piece. The cutting inserts are typically clamped or screw-mounted into pockets present around the periphery of the cutter body. Since the pockets have to conform in part to the shape of the inserts to adequately stabilize them during a cutting operation, such milling cutters are limited in the number of types of inserts that they can use.

In order to overcome the above problem, replaceable tool cartridges have been developed in milling cutters. In such cutters, the cutting inserts are retained in a pocket present on the leading face of a tool cartridge which in turn are detachably mounted in recesses in the cutter body.

Similarly, in developing boring bar equipment it is desirable to provide rapid adjustment of indexable inserts without sacrificing accuracy due to traverse bar loading. With respect to boring bar equipment, cartridge tools are affixed to the periphery of a boring bar by screws, clamps, or wedges and which focus on the tolerance problem by affording adjustment, wherein the cartridges provide adjustment for cutting inserts.

Conventionally, during material removal operations, both milling and turning, utilizes ISO inserts, and also brazed type inserts such as tungsten carbide cutting tool inserts, PCD (Polycrystalline Diamond) inserts, CBN (Cubic boron nitride) inserts are used for cutting edges and held on holder by cartridges for clamping on the main body.

The brazed type milling cutters are directly brazed on the body of milling cutter or boring, wherein the adjustment may not be possible for run out or size on individual cutting edges. Presently, square/rectangular shaped cartridges are designed and used at present by many manufacturers with the design holding on the body of cutter by providing rectangular hole in the center of cartridges and clamping it by bold to hold with the cutter, and also height adjustment by a screw in the back side of the cartridge.

A conventional milling cartridge 100a is shown in FIG. 1.1, where in the milling cartridge includes a body 101 in rectangular shape having an elliptical bolting hole 102 for locking the cartridge using a bolt and to accommodate axial movement of the cartridges, a height setting screw 103 for adjustment and an insert 104. Another prior art cartridge 100b is shown in FIG. 1.2, which is specially developed for PCD and CBN application, and its body 101 is also in rectangular shape, locked by a bolt 105 and locked in central elliptical shaped hole 102 in the cartridge 100b. Further, the cartridge 100b is adjusted by using a height setting screw 105, wherein the adjustment would be possible only in one direction for the height of cartridges and hence the cutting edge.

In the conventional cartridges, the locking bolt hole is provided in oval shape to accommodate the height adjustment of cartridges. Moreover, the bolt hole is provided in the center of the cartridge which may weaken the cartridge. Therefore, the design of cartridge size becomes larger and can add limitation of reducing the size of the cartridges. In general, the shape of the cartridges is either square or rectangular in shape, which may lead to difficulty in achieving the accuracy in cartridge size, and also the location pocket of the cartridges can be finished only by milling operation, which is very difficult to get the accuracy from center of the cutter.

Another drawback of conventional cartridges is height adjustment can be made only in one direction, particularly cartridge can be moved only in the upward direction by rotating the screw in one direction while setting, and in case it crosses a particular limit, then the locking bolt needs to be loosened manually, brought back and once again the setting procedure needs to be repeated. Hence, it is a time consuming process and not very accurate.

Yet another drawback is that there is no location guide for locating the cartridge in same position while either changing the cartridge or replacing the cartridges and the accuracy may suffer. Especially, the milling cutter cartridges can be set or adjusted in presetter only. Therefore, the cartridges after assembling with the spindle are not possible to adjust or set which is a major drawback of the existing cartridge system.

Therefore there remains a need in the art to develop an improved cartridge in cylindrical shape for locking rigidly. Further, such cartridge design should allow to reduce the size as well allow to adjust in both direction, so that the setup time can be reduced drastically.

OBJECTS OF THE INVENTION

Some of the objects of the present disclosure are described herein below:

The main object of the present invention is to provide a simple rigid and accurate cylindrical cartridge which can used for universal holding system, particularly in milling cutters and boring bars.

Another object of the present invention is to provide a cartridge in cylindrical shape for easy manufacture and also to maintain the size of cartridge as needed.

Yet another object of the present invention is to provide a cartridge which can move in forward and backward direction, thus face run out can be controlled very close to 3 micron.

Still another object of the present invention is to provide a cartridge which can able to control the positioning accuracy within 10 micron thus run out on multiple cutting edges on the cutter can be controlled up to 10 micron.

Another object of the present invention is to provide a cartridge which can be compact thus to increase the number of cutting edges in cartridge system.

Another object of the present invention is to provide a cartridge to increase the speed and feed of cutting tools to reduce the cycle time and with high quality of surface finish and accuracy.

Another object of the present invention is to provide a cartridge system for easy, accurate in assembling and setting of the cartridges.

Another object of the present invention to provide a marking on cutter body measuring/controlling the movement distance of cartridges accurately.

The other objects and advantages of the present invention will be apparent from the following description when read in conjunction with the accompanying drawings which are incorporated for illustration of preferred embodiments of the present invention and are not intended to limit the scope thereof.

SUMMARY OF THE INVENTION

In view of the foregoing, an embodiment herein discloses a rigid cartridge for multiple and universal application of all machining processes. The rigid cartridge includes a cylindrical body, a guiding & locating body connected to bottom side of cylindrical body, and a combination screw having a left hand [LH] thread and a right hand [RH] thread, wherein the cylindrical body includes a flat for locking the cartridge with the cutter body by using a locking screw, wherein the combination screw is connected to the bottom end of the guiding & locating body. The diameter of the guiding & locating body is provided lesser than the cylindrical body for guiding the cartridge axially on accurate concentric pocket made in the body within 20 micron clearances. The guiding & locating body can be made in any shape including but not limited to cubical, hexagonal, and triangular.

In an embodiment, a central hole can be provided in the combination screw for rotating the screw in a desired direction. The combination screw is provided with center hole between LH thread and RH thread. The LH thread is provided in cartridge side and RH thread is provided in cutter body side or vice versa.

In the cutter body or boring bar, a slot or an approach hole can be provided for enabling to rotate the combination screw in clockwise or anti-clockwise direction to move the cartridge in forward and/or backward direction. Further, a threaded locking hole can be provided in the cutter body for locking the cartridge with the cutter body by using a grub screw. The bottom surface of the slot can be provided with marking in degrees for measuring/controlling the movement distance of cartridges accurately.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The detailed description is set forth with reference to the accompanying figures. In the figures the use of the same reference numbers in different figures indicates similar or identical items.

FIGS. 1.1 and 1.2 illustrate a conventional cartridge used in milling cutters.

DETAILED DESCRIPTION OF THE PREFERRED EMBODIMENTS

Figure 2:
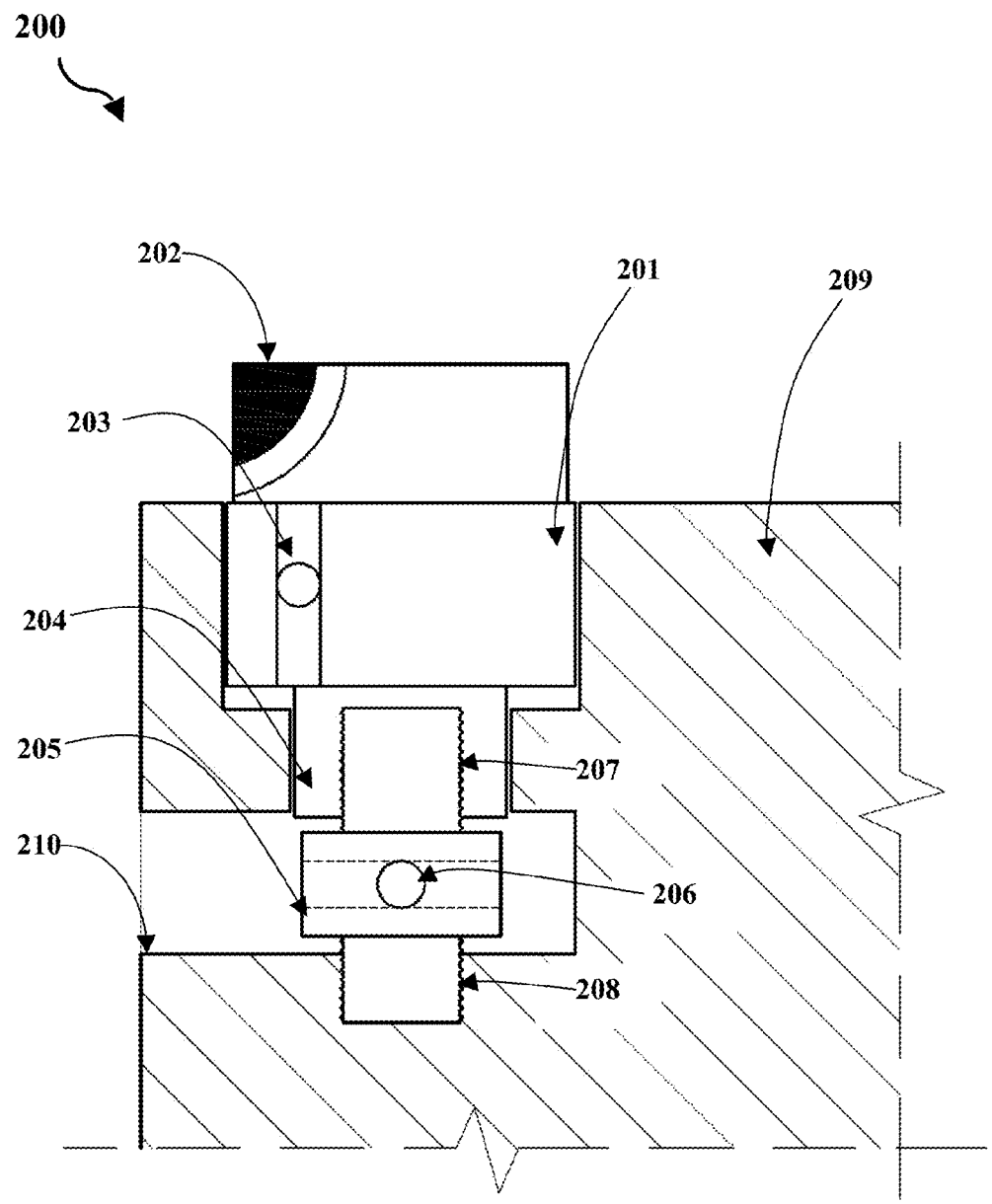
FIG. 2 illustrates a cross section view of a cartridge placed in milling cutter, according to an embodiment herein.

The embodiments herein and the various features and advantageous details thereof are explained more fully with reference to the non-limiting embodiments and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for developing a cartridge which can be manufactured at reduced size as well to adjust in forward and backward direction, so that the setup time can be reduced drastically and also can be positioned accurately. Referring now to drawings, and more particularly to FIGS. 2 through 4, where similar reference characters denote corresponding features consistently throughout the figures, there are shown preferred embodiments.

Now referring to FIG. 2, a cross sectional view 200 of a cartridge locked in milling cutter 209 is illustrated according to an embodiment of the present invention. Accordingly, the cartridge 200 includes a cylindrical body 201, a guiding & locating body 204 connected to bottom side of cylindrical body 201, and a combination screw 205 having a left hand [LH] thread 207 and a right hand [RH] thread 208, wherein the cylindrical body 201 includes a flat 203 for locking the cartridge 200 with the cutter 209 by using a locking screw [not shown]. Further, the combination screw 205 can be connected to the bottom end of the guiding & locating body 204. In a further embodiment, the cartridge 200 is provided with an arrangement for holding an insert 202 which can cut the work pieces and/or bore. The guiding & locating body 204 can be made in any shape including but not limited to cubical, hexagonal, and triangular.

According to an embodiment, the diameter of the guiding & locating body 204 is provided lesser than the cylindrical body 201 for guiding the cartridge 200 axially on accurate concentric pocket made in the body 209 within 20 micron clearances. Further, the guiding & locating body 204 can secure the positional accuracy of the cutting edge as it is made parallel to the cutting edge, control the center height of the cutting edge and restrict the rotation of the cartridge while in operation.

In an embodiment, a central hole 206 can be provided in the combination screw 205 for rotating the screw 205 in a desired direction. In another embodiment, a spanner holding portion [not shown] can be provided in the combination screw 205 for rotating the screw 205. In yet another embodiment, the central hole 206, preferably an allen head hole 206 can be provided from bottom end of the combination screw 205, in order to rotate the combination screw 205 in a desired direction and to move the cartridge 200 in forward/backward direction. Accordingly, an approach hole (not shown) can be provided in the cutter body below the combination screw to provide access for an allen key. The allen key can be used to connect with the allen head hole 206 to rotate the combination screw 205 from the bottom side of combination screw 205. In another embodiment, the combination screw 205 can be provided with center hole 206 between LH thread 207 and RH thread 208. In an embodiment, the LH thread 207 can be provided in cartridge 200 side and RH thread 208 can be provided in cutter body 209 side or vice versa. With the help of combination screw 205, the combination screw 205 can be rotated in clockwise or anti-clockwise rotation, which enables to move the cartridge 200 in forward and backward direction. Further, the combination screw 205 can maintain the positional accuracy of cartridges and can lock the cartridge rigidly.

Figure 3:
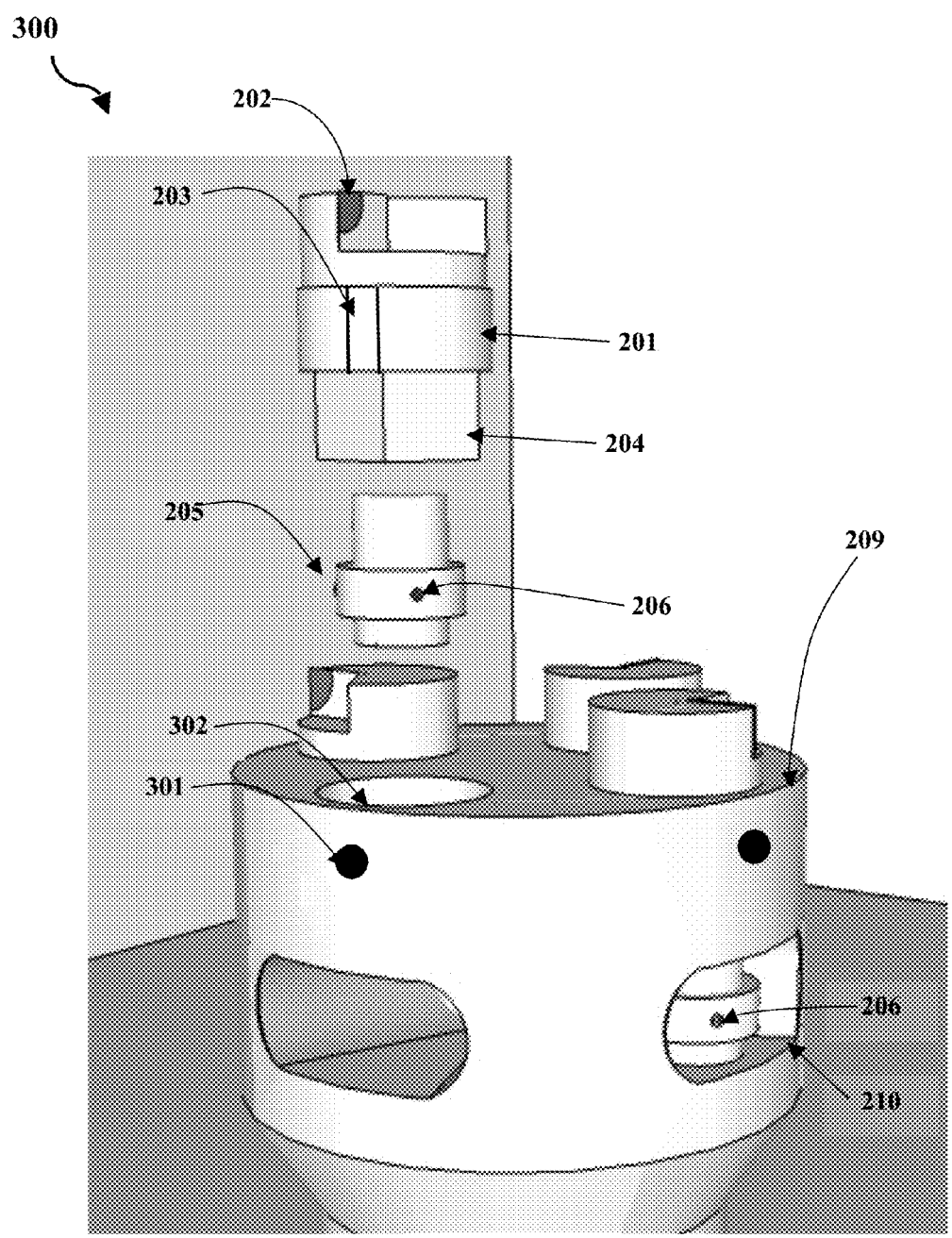
FIG. 3 illustrates a perspective view of plurality of cartridges locked in pockets of milling cutter, according to an embodiment herein.

According to an embodiment, a perspective view 300 of plurality of cartridges 200 locked in pockets of milling cutter 209 is illustrated in FIG. 3. In an embodiment, a slot 210 can be provided on the cutter body 209 or boring bar [not shown] for enabling to rotate the combination screw in clockwise and anti-clockwise direction. Since the cartridge 200 body is provided in cylindrical shape, the locking surface size can be controlled upto h6, tolerances and locating hole can be maintained H6 tolerances. Radial run out depends on positional accuracy of the threaded locking hole 301 which can be very easily achieved by reaming or gig boring of cartridge bore of the cutter/boring bar. Therefore, the radial run out can be controlled precisely within 10 microns.

Figure 4:
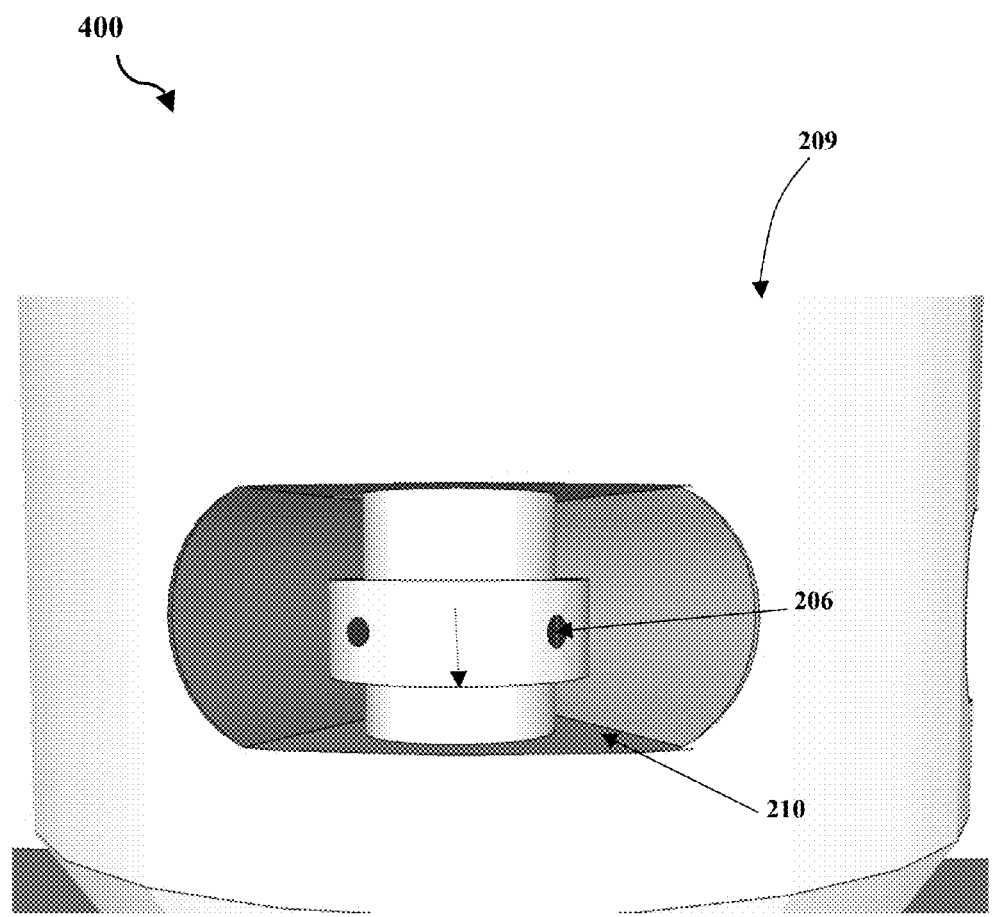
FIG. 4 illustrates a front view of arrangement provided in cutter body for height adjustment of cartridges, according to an embodiment herein.

Now to referring to FIG. 4, a front views 400 of arrangement provided in cutter body 209 for height adjustment of cartridges 200 is illustrated according to an embodiment. Accordingly, the slot 210 and/or approach hole [not shown] provided in the cutter body 209 enables to rotate the combinational screw 205 with the help of center hole 206 and/or allen hole head provided in the screw 205. The bottom surface of the slot 210 can be provided with marking in degrees [not shown] for measuring/controlling the movement distance of cartridges 200, according to an embodiment. Therefore, movement of the cartridge can be controlled with respect to marking between the holes or marking on every 90 deg. on periphery of LH and RH screw, which can be accurately noted and also controlled for micro movement of the cutting edges. Further, the axial movement of the cartridge can be controlled within 2 microns.

Figure 5:
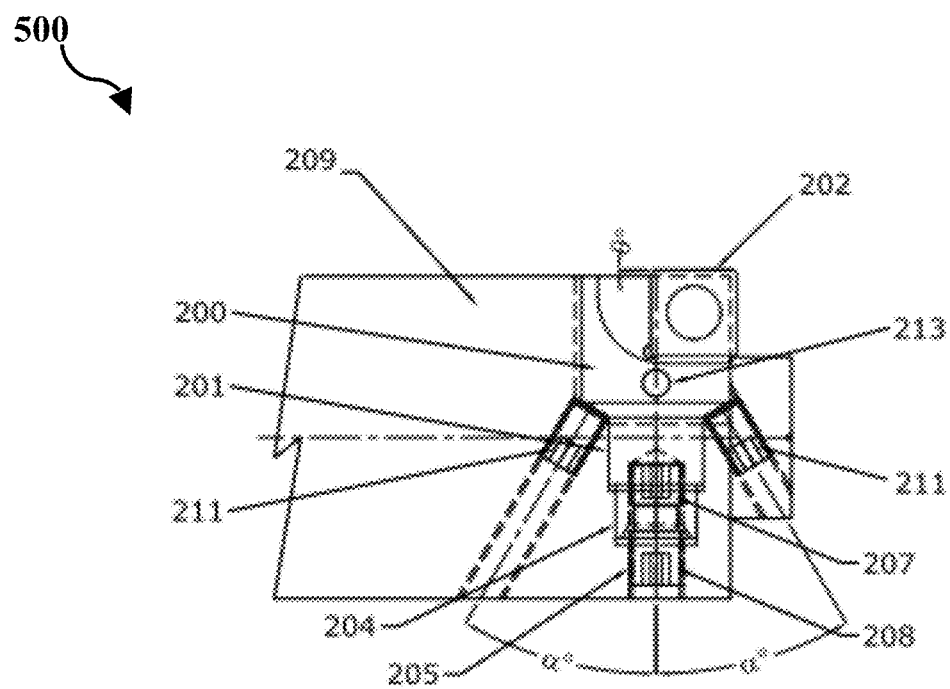
FIG. 5 illustrates a cross sectional view of arrangement provided in improved cutter body for back tapering on the cutting edge, according to an embodiment herein.

Now referring to FIG. 5, a cross sectional view 500 of arrangement provided in improved cutter body to achieve back tapering on cutting edge with two grub screws in the cutter body is illustrated according to an embodiment. According to the embodiment, the cylindrical body and guiding and locating body of the cartridges are assembled in the cutter body 209. The cylindrical body and guiding and locating body can be moved upwards by rotating the LH & RH screw by clockwise direction. When the LH & RH screw is rotated in anti clockwise than the cartridge can be moved downward and vice versa. Once the designed height is reached, the cartridge can be locked in position by locking screw at top 212 and bottom 213. In order to achieve the back taper on cutting edge, another two grub screws 211 are mounted at a degree $\alpha°$ to the cartridge centre line. This angle $\alpha$ can be 10°-90° depending on the required design. By tightening the screw upward as required to adjust the angle, then the cartridge can be moved the cartridge in any desired angle. Once the required back taper $\theta°$ is achieved, then the other screws can be locked in position. Hence the cutting edge on the top and back taper angle $\theta°$ can be maintained as per the design from 0°-5°. Here the insert 202 can be made of any material including but not limited to brazed PCD, CBN or carbide. Maximum tilting angle can be controlled by the clearance given in the cylindrical body as designed for reaming, boring or grooving applications. These grub screws 211 not only tilt the cutting edge angle also help to hold the cartridge rigidly in position and also reduce vibration during cutting.

Figure 5A:
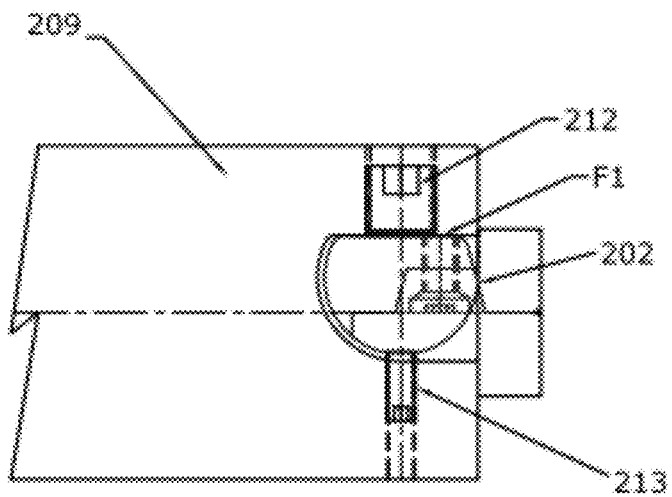
FIG. 5A illustrates a top view of arrangement provided in improved cutter body for back tapering on the cutting edge, according to an embodiment herein.

Now referring to FIG. 5A, a top view 501 of arrangement provided in improved cutter body for back tapering on the cutting edge according to the embodiment. Designing for the reamer cartridges, grooving, chamfer and plunge cutting applications, height adjustment of the cutting edge can be achieved by existing system. But back taper on the cutting edge is also important and controlling after assembly is also essential. This can be achieved by making modification on the cartridge design without altering the basic original principle.

Figure 6:
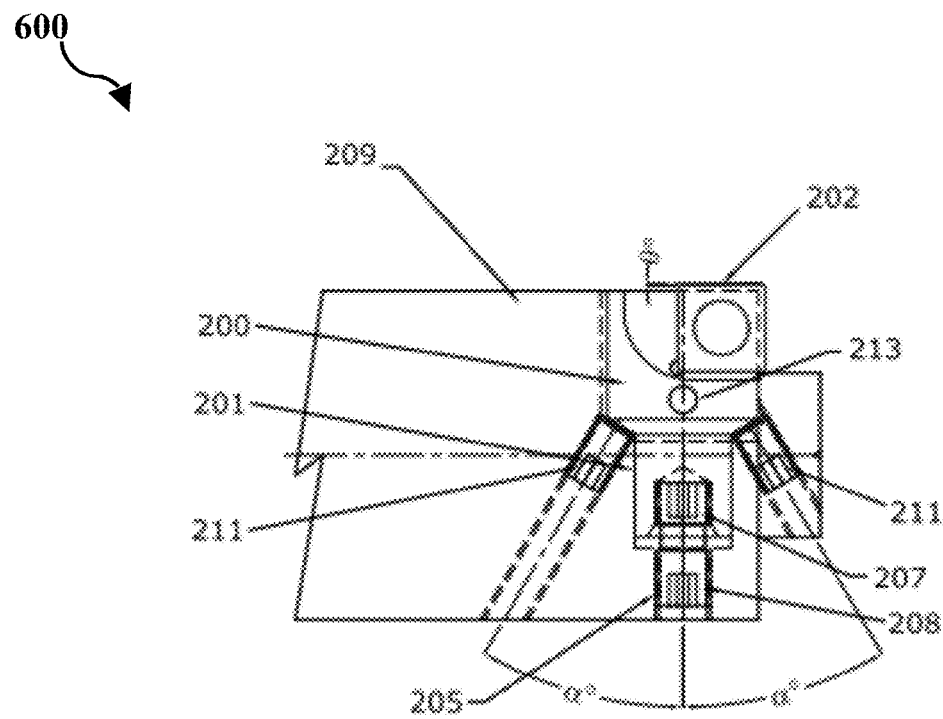
FIG. 6 illustrates a cross sectional view of arrangement provided in improved cutter body for back tapering on the cutting edge and for facilitating anti-rotation, according to an embodiment herein.

Now referring to FIG. 6, cross sectional view 600 of arrangement provided in improved cutter body for back tapering on the cutting edge and for facilitating anti-rotation. The basic principal of cartridge is same with cylindrical body and LH & RH Screw when rotated clockwise then the cartridge may move upwards and anti clock wise rotation may move the cartridge downward. After reaching the designed height, the position can be locked by locking screw 213 at the bottom. The two grub screws 211 are provided at $\alpha°$ angle and which may vary from 10° to 90° to adjust the angle 0° of the cutting edge as per the design from 0° to 5°. Here guiding and locating body position 204 in the cartridge zone can be removed to facilitate anti rotation of the cartridge. The cartridge is made flat parallel to cutting edge and corresponding counter is made on the cutter body 209. Designed height depends on cutting edge centre height. When cartridge is tightened by locking screw 213, cartridge bottom may butt to body on bottom face F1 and can hold the cartridge in position as act as anti rotation and may perform the same function of guiding and locating body 204. The above mentioned design without guiding and locating body 204 can make the cartridge design simple and further the cartridge height can be reduced. This type of cartridge can be designed for the small sizes of reamers, boring bars, grooving and plunging operations etc.

Figure 6A:
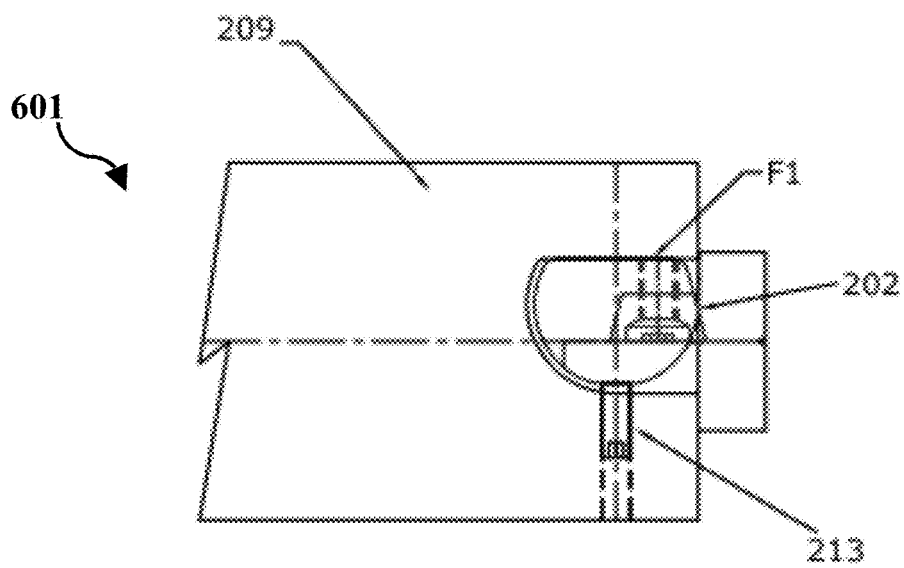
FIG. 6A illustrates a top view of arrangement provided in improved cutter body for back tapering on the cutting edge and for facilitating anti-rotation, according to an embodiment herein.

Now referring to FIG. 6A, top view 601 of arrangement provided in improved cutter body for back tapering on the cutting edge and for facilitating anti-rotation. In the top view, the position of the insert 202 and the locking screw 213 is provided without the guiding and locating body 204.

Figure 7:
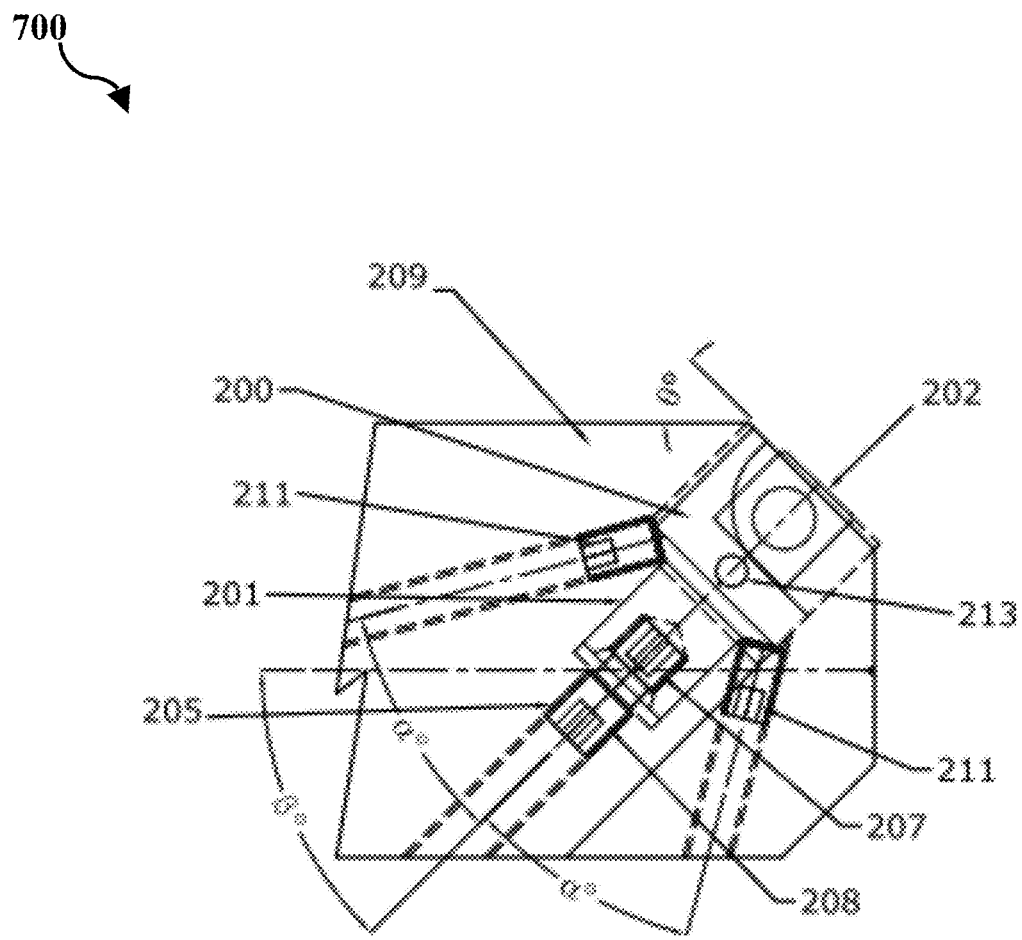
FIG. 7 illustrates a cross sectional view of improved cutter body with radially adjustable center axis, according to an embodiment herein.

Now referring to FIG. 7, a cross sectional view 700 of an improved cutter body with radially adjustable center axis. For other applications such as plunge operations, cartridge centre axis can be mounted in any degree to the centre axis of the body as per the tool design. The centre axis of the cutter body 209 may vary from 0°-90°. The same design as discussed in FIG. 6 is applied with radially adjustable center axis for plunge operation.

Exemplary Assembling of Cartridges:

Initially, the cartridge 200 is assembled outside the cutter body 209. The cartridge 200 is connected with the combinational screw 205 with ¾ length of screw inside the cartridge 200. Further, the cartridge 200 is inserted in the pocket 302 and assembled by rotating the screw 205 in clockwise direction. Care needs to be taken that the cutting edge of the cartridge 200 is facing outwards. After fixing the cartridge in pockets with the adjustment of combinations screw 205, the cartridge 200 is locked securely by a locking screw [not shown] inserted through the locking 301 into the flat 203 provided in cartridge 200. Thereafter, once again the combination screw 205 is slightly tightened to maintain the proper tension of cartridge 200 with the cutter body 209.

In another embodiment, with slight modification and providing collar or step in the cartridge 200 for face butting, cartridge can be locked securely. Accordingly, the combination screw 205 is tightened till the cartridge face is butting properly with the face without any gap. Thereafter, the locking screw is tightened to secure the cartridge in position. This can be used for modular locking and series connection of multiple holders in long boring bars.

A main advantage of the present invention is the cartridges are designed in cylindrical in shape hence it can be designed with very small size. In multi-point milling cutters and boring bars, the cartridges can be designed to accommodate in larger number of cartridges for a particular diameter. Accordingly, it would lead to increase the feed rate and can be achieved drastic reduction in cycle time of particular operation and increase in productivity.

According to present invention, the cartridges can be used for multiple applications including milling cutter, boring bars, guide pad type reamers and modular holding. In guide pad type reamers, the invented cartridge can be used instead of cutting blade for achieve the same accuracy and finish. Further, the cartridges can be made in steel, heavy material, and also directly in carbide with the provision of threaded hole by brazing steel material. Accordingly, it can improve the rigidity of the milling cutters and borings bars. Further, the invented cartridges can be used for multiple and universal application of all machining processes including milling, boring, reaming, modular holders, extension bars as per the tool design and application.

According to present invention, the cartridges are simple in design, rigid, and are also possible to adjust in micron level with close control on run out and can be used universally in multiple applications which can improve the quality as well as the cost of manufacturing processes which is the need of today's manufacturing industry.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A rigid cartridge holding system, comprises of a cartridge and a cutter body, wherein said cartridge includes a cylindrical body, a guiding and locating body connected to a bottom side of the cylindrical body, an insert provided on top of the cylindrical body for cutting work pieces, at least two grub screws and a combination screw having a left hand [LH] thread and a right hand [RH] thread provided with same pitch;

wherein said cylindrical body includes a flat for locking said cartridge with said cutter body using a locking screws provided at bottom and top of the cylindrical body;

wherein a slot is provided in said cutter body for enabling to access the combination screw thereby enabling to rotate said combination screw in clockwise or anti-clockwise direction for height adjustment of said cartridge particularly to move said cartridge in forward or backward direction with respect to the cutter body.

2. The rigid cartridge holding system as claimed in claim 1, wherein said two grub screws are mounted at a degree α to the cartridge centre line.

3. The rigid cartridge holding system as claimed in claim 2, wherein said degree α are in the range of 10°-90°.

4. The rigid cartridge holding system as claimed in claim 1, wherein said insert is having a back taper angle θ°.

5. The rigid cartridge holding system as claimed in claim 1, wherein tightening of said grub screws in the cartridge enables to tilt said insert to achieve the back taper angle θ°.

6. The rigid cartridge holding system as claimed in claim 1, wherein said two grub screws are tightened to hold the cartridge rigidly in position and to reduce vibration of the insert during cutting.

7. The rigid cartridge holding system as claimed in claim 1, wherein said insert is made of brazed PCD or CBN or carbide.

8. The rigid holding system as claimed in claim 1, wherein diameter of the guiding and locating body is lesser than the cylindrical body for guiding the cartridge axially, wherein the guiding and locating body is provided with maximum 20 micron clearance from accurate concentric pocket provided in the cutter body.

9. The rigid cartridge holding system as claimed in claim 8, wherein outer shape of the guiding and locating body is cubical or hexagonal or triangular.

10. A rigid cartridge holding system, comprises of a cartridge and a cutter body, a cylindrical body, an insert provided on top of the cylindrical body for cutting work pieces, at least two grub screws, and a combination screw having a left hand [LH] thread and a right hand [RH] thread provided with same pitch;

wherein said cylindrical body includes a flat for locking said cartridge with the cutter body using locking screws provided at top and bottom of the cylindrical body;

wherein a slot is provided in said cutter body for enabling to access the combination screw thereby enabling to rotate said combination screw in clockwise or anti-clockwise direction for height adjustment of said cartridge particularly to move said cartridge in backward or forward direction with respect to the cutter body.

* * * * *